United States Patent
Kokubo (10) Patent No.: US 10,116,848 B2
(45) Date of Patent: *Oct. 30, 2018

(54) ILLUMINATION AND IMAGING SYSTEM FOR IMAGING RAW SAMPLES WITH LIQUID IN A SAMPLE CONTAINER

(71) Applicant: SCREEN HOLDINGS CO., LTD., Kyoto (JP)

(72) Inventor: Masahiko Kokubo, Kyoto (JP)

(73) Assignee: Screen Holdings Co., Ltd., Kyoto (JP)

( * ) Notice: Subject to any disclaimer, the term of this patent is extended or adjusted under 35 U.S.C. 154(b) by 49 days.

This patent is subject to a terminal disclaimer.

(21) Appl. No.: 15/248,555

(22) Filed: Aug. 26, 2016

(65) Prior Publication Data

US 2017/0257539 A1 Sep. 7, 2017

(30) Foreign Application Priority Data

Mar. 1, 2016 (JP) .................................. 2016-039259

(51) Int. Cl.
*H04N 5/225* (2006.01)
*G01N 33/487* (2006.01)
(Continued)

(52) U.S. Cl.
CPC .......... *H04N 5/2256* (2013.01); *C12M 23/12* (2013.01); *C12M 23/22* (2013.01); *C12M 41/36* (2013.01); *G01N 21/253* (2013.01); *G01N 21/84* (2013.01); *G01N 33/487* (2013.01); *G02B 21/0032* (2013.01); *G02B 21/0088* (2013.01); *G02B 21/086* (2013.01); *G02B 21/362* (2013.01);
(Continued)

(58) Field of Classification Search
CPC .. H04N 5/2256; G01N 33/487; G02B 21/362; G02B 21/0032; G06K 9/00134
See application file for complete search history.

(56) References Cited

U.S. PATENT DOCUMENTS

| 9,069,175 B2 | 6/2015 | Koebler et al. |
| 2012/0068059 A1* | 3/2012 | Montes Usategui .. G02B 21/32 250/251 |

(Continued)

FOREIGN PATENT DOCUMENTS

| EP | 1742064 | 1/2007 |
| JP | 2012-147739 | 8/2012 |

(Continued)

OTHER PUBLICATIONS

Extended European Search Report issued in corresponding EP Patent Application No. 16186593.6, dated Jun. 8, 2017.

(Continued)

*Primary Examiner* — Shahbaz Nazrul
(74) *Attorney, Agent, or Firm* — McDermott Will & Emery LLP (57) ABSTRACT

An illuminator includes a light source and an illumination optical system for causing light emitted from the light source to be incident on a sample surface where an imaging object is present. The illumination optical system has an optical axis coaxial with that of an imaging optical system. An image of the light source is formed between the illumination optical system and the imaging optical system. A holder arranges the sample surface between the light source image and the imaging optical system.

10 Claims, 9 Drawing Sheets

(51) Int. Cl.
    G02B 21/36    (2006.01)
    G06K 9/00     (2006.01)
    G01N 21/25    (2006.01)
    G02B 21/00    (2006.01)
    G02B 21/08    (2006.01)
    G01N 21/84    (2006.01)
    C12M 1/32     (2006.01)
    C12M 1/00     (2006.01)
    C12M 1/34     (2006.01)

(52) U.S. Cl.
    CPC .......... *G06K 9/00134* (2013.01); *G02B 21/36* (2013.01)

(56) References Cited

U.S. PATENT DOCUMENTS

| | | | |
|---|---|---|---|
| 2013/0076897 A1 | 3/2013 | Ogi et al. | |
| 2013/0259334 A1* | 10/2013 | Otsuka | G06T 7/0012 382/128 |
| 2013/0280748 A1 | 10/2013 | Gebetsroither et al. | |
| 2013/0293706 A1 | 11/2013 | Pison et al. | |
| 2014/0099659 A1* | 4/2014 | Keller | G01N 21/6486 435/29 |
| 2014/0104681 A1* | 4/2014 | Berman | G02B 21/0032 359/385 |
| 2014/0160267 A1* | 6/2014 | Kawakami | G02B 21/244 348/79 |
| 2016/0131885 A1* | 5/2016 | Nakayama | G01N 21/6428 250/458.1 |
| 2016/0139388 A1* | 5/2016 | Asundi | G02B 26/06 348/79 |

FOREIGN PATENT DOCUMENTS

| | | |
|---|---|---|
| JP | 2015-118036 A | 6/2015 |
| WO | 2015/093344 A1 | 6/2015 |

OTHER PUBLICATIONS

Extended European Search Report issued in corresponding European Patent Application No. 16186606.6, dated Jul. 20, 2017.

* cited by examiner

ILLUMINATION AND IMAGING SYSTEM FOR IMAGING RAW SAMPLES WITH LIQUID IN A SAMPLE CONTAINER

CROSS REFERENCE TO RELATED APPLICATION

The disclosure of Japanese Patent Applications enumerated below including specification, drawings and claims is incorporated herein by reference in its entirety: No. 2016-39259 filed Mar. 1, 2016.

BACKGROUND OF THE INVENTION

1. Field of the Invention

This invention relates to a technique for imaging raw samples carried together with liquid in a sample container and particularly relates to the illumination of the raw samples.

2. Description of the Related Art

In medical and bioscience experiments, liquid or gel-like fluid (e.g. culture fluid, culture medium or the like) is poured into each well of a plate-like sample container (e.g. called a microplate, a microtiter plate or the like) on which a multitude of recesses, for example, also called wells are arranged, and cells and the like cultured here are observed and measured as samples. In recent years, samples have been imaged and converted into data by a CCD camera or the like, and various image processing techniques have been applied to this image data for observation and analysis.

In such an imaging apparatus, there is a problem that illumination light is refracted by the meniscus of a liquid surface and the brightness of an image becomes insufficient particularly at peripheral edge parts of the wells. To deal with this problem, in a technique described in JP 2015-118036A previously disclosed by the applicant of this application, an imaging optical system has an object-side hypercentric property, whereby light having a propagation direction bent in a direction away from an optical axis by refraction can be efficiently collected.

SUMMARY OF THE INVENTION

To observe finer structures, it is considered to set a higher imaging magnification of the imaging optical system. Further, the wells used come in various sizes. In these cases, there are cases where an area with the influence of the meniscus is included in an imaging field of view and cases where such an area is not included, particularly if an imaging field of view becomes smaller than one well. When the area without the influence of the meniscus is imaged, a light quantity is reduced in a peripheral edge part of the imaging field of view in imaging using the imaging optical system described above and an effective imaging field of view may become narrower.

This invention was developed in view of the above problem and aims to provide a technique capable of obtaining an image with good image quality even in the absence of the influence of meniscus using an imaging optical system taking into account the influence of the meniscus in a technique for imaging a raw sample carried together with liquid in a sample container.

According to an aspect of the disclosure, there is provided an imaging apparatus that images a raw sample as an imaging object carried together with liquid in a sample container with a bottom surface having optical transparency. The apparatus comprises: a holder that holds the sample container; an imaging optical system, arranged to face the sample container held by the holder, that has an object-side hypercentric property; an imaging element that images an image of the imaging object focused by the imaging optical system; and an illuminator that illuminates the imaging object from a side opposite to the imaging optical system across the sample container held by the holder, wherein: the illuminator includes a light source and an illumination optical system that causes light emitted from the light source to be incident on a sample surface where the imaging object is present; the illumination optical system has an optical axis coaxial with that of the imaging optical system and an exit pupil position located between the illumination optical system and the imaging optical system; and the holder arranges the sample surface between the exit pupil position and the imaging optical system.

In the invention thus configured, light emitted from the illumination optical system is incident on the sample surface after passing through the exit pupil position. Thus, a beam having components in directions away from the optical axis of the imaging optical system is incident on the sample surface. On the other hand, the imaging optical system has the object-side hypercentric property capable of guiding the beam having such components in the directions away from the optical axis of the imaging optical system and emitted from the sample surface to the imaging element. Accordingly, the raw sample without the influence of meniscus can be imaged with good image quality by combining the illumination optical system and the imaging optical system as described above.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DETAILED DESCRIPTION OF THE PREFERRED EMBODIMENTS

Figure 1:
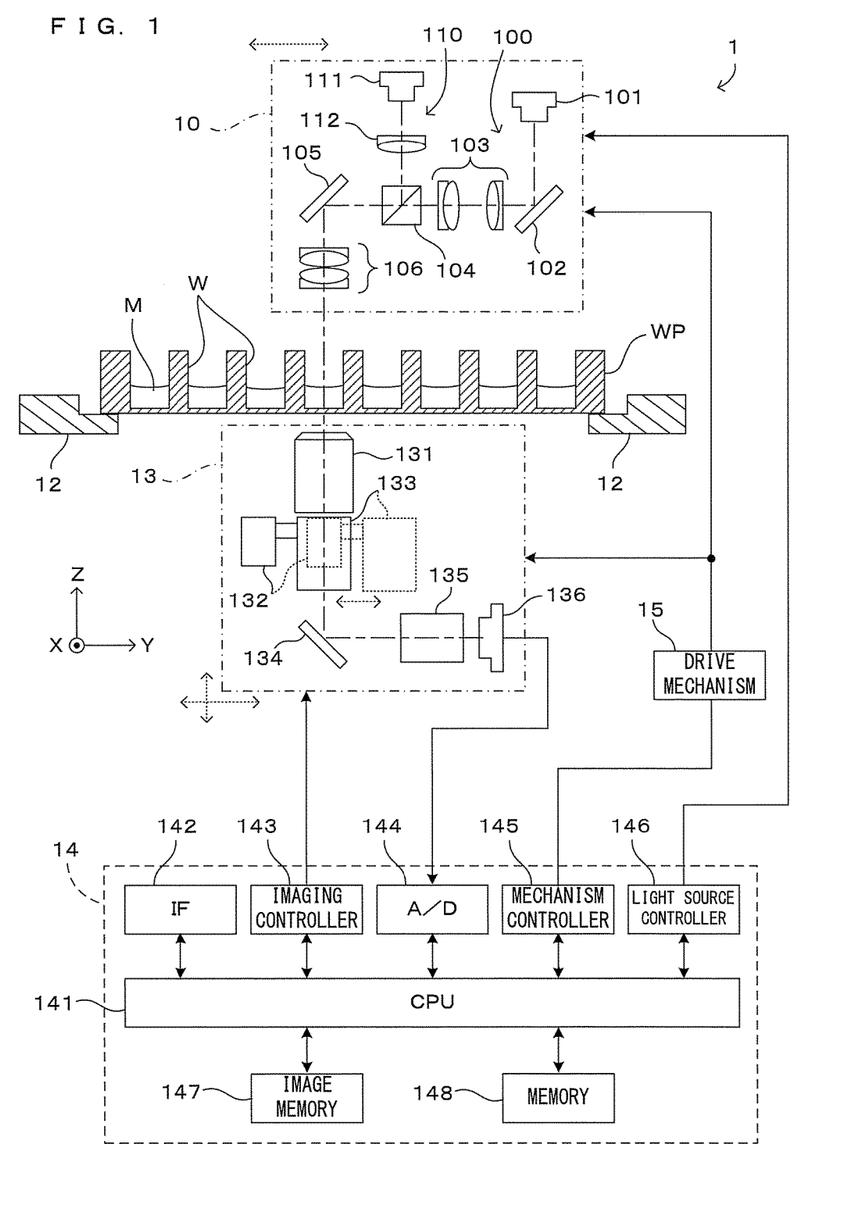
FIG. 1 is a diagram showing a schematic configuration of one embodiment of an imaging apparatus according to the invention.

FIG. 1 is a diagram showing a schematic configuration of one embodiment of an imaging apparatus according to the invention. This imaging apparatus is an apparatus for imaging raw samples such as cells, cell colonies and bacteria (hereinafter, referred to as "cells and the like") cultured in liquid poured into recesses called wells W formed on the upper surface of a well plate WP.

The well plate WP is generally used in the fields of drug discovery and bioscience. The well plate WP has a flat plate shape and a plurality of tubular wells W having openings on the upper surface of this plate are arranged on the well plate WP. Each well W has, for example, a substantially circular cross-section and a bottom surface is transparent and flat and has optical transparency. The cross-section and the bottom surface shape of the well W are not limited to these. For example, the cross-section may be rectangular and the bottom surface may be curved.

The number of the wells W on the well plate WP is arbitrary. For example, a well plate WP having 96 (12×8 matrix array) wells can be used. A diameter and a depth of each well W are typically about several mm. Note that the size of a well plate and the number of wells used in this imaging apparatus 1 are arbitrary without being limited to these. For example, well plates having 6 to 384 wells are generally used. Further, without limitation to well plates having a plurality of wells, this imaging apparatus 1 can be used, for example, also for imaging of cells and the like cultured in a flat container called a dish.

A predetermined amount of liquid as a culture medium M is poured into each well of the well plate WP, and the cells and the like cultured under predetermined culture conditions in this liquid are imaging objects of this imaging apparatus 1. The culture medium M may be added with appropriate reagents or may be gelled after being poured into the wells W in a liquid state. As described later, in this imaging apparatus 1, cells and the like cultured on the inner bottom surfaces of the wells W can be, for example, imaging objects. About 50 to 200 microliters of the liquid is generally usually used.

The imaging apparatus 1 includes an illuminator 10 arranged in an upper part of the apparatus 1, a holder 12 for holding the well plate WP below the illuminator 10, an imager 13 arranged below the holder 12 and a controller 14 with a CPU 141 for controlling the operation of each of these parts. The holder 12 holds the well plate WP in a substantially horizontal posture by being held in contact with a peripheral edge part of the lower surface of the well plate WP carrying samples together with the medium M in each well W.

The illuminator 10 includes two light sources 101, 111. For example, white LEDs (Light Emitting Diodes) can be used as the light sources 101, 111. Light emitted from the light source 111 is incident on a beam splitter 104 via a collector lens 112. On the other hand, light emitted from the light source 101 has an optical path reflected by a reflection mirror 102 and is incident on the beam splitter 104 via a collector lens 103. A beam emitted from the beam splitter 104 has a propagation direction changed to a (-Z) direction, i.e. a vertically downward direction by a reflection mirror 105 and is emitted downward via a condenser lens 106. The emitted light is incident on at least one well W from above the well plate WP supported on the holder 12 to illuminate imaging objects in the well W.

As just described, in the illuminator 10 of this embodiment, two illumination optical systems, i.e. a first illumination optical system 100 using the light source 101 as a light source thereof and composed of the reflection mirror 102, the collector lens 103, the beam splitter 104, the reflection mirror 105, the condenser lens 106 and the like and a second illumination optical system 110 using the light source 111 as a light source thereof and composed of the collector lens 112, the beam splitter 104, the reflection mirror 105, the condenser lens 106 and the like coexist while sharing some constituent components.

The light sources 101, 111 are controlled to be turned on and off by a light source controller 146 provided in the controller 14 and selectively turned on in accordance with a control signal from the light source controller 146. Thus, the illuminator 10 can cause first illumination light emitted from the first illumination optical system 100 including the light source 101 and second illumination light emitted from the second illumination optical system 110 including the light source 111 to be selectively incident on the well W. The first illumination light and the second illumination light are guided through the beam splitter 104 and these can be coaxially emitted. Specifically, center axes of the first illumination light and the second illumination light emitted from the condenser lens 106 coincide.

Figure 2:
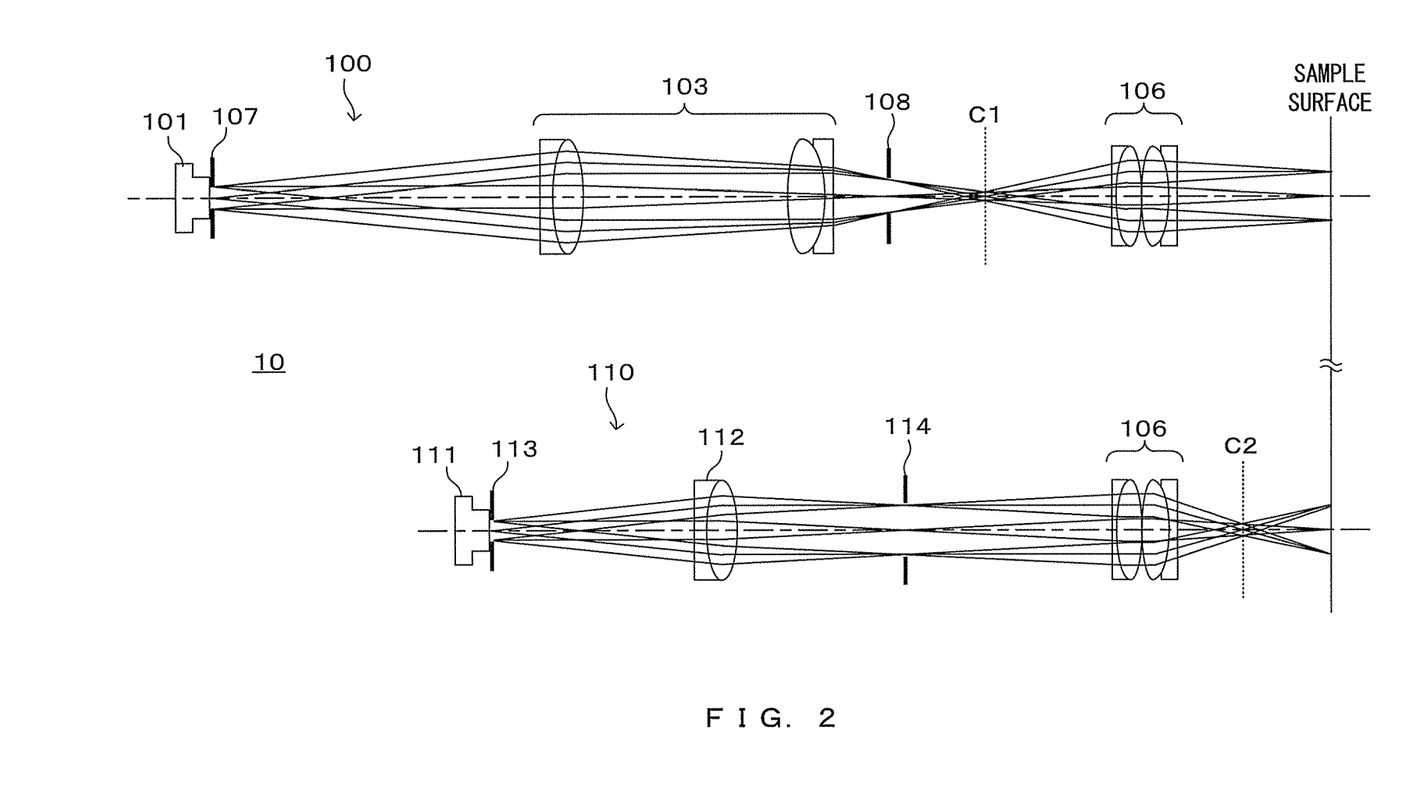
FIG. 2 is a diagram showing detailed configurations and ray diagrams of the illumination optical systems.

FIG. 2 is a diagram showing detailed configurations and ray diagrams of the illumination optical systems. In FIG. 2, the first and second illumination optical systems 100, 110 sharing some constituent components as described above are separately shown to clearly show optical paths. Further, for the same purpose, the optical axes bent by the reflection mirrors and the beam splitter is shown to be straight. Thus, the reflection mirrors 102, 105 and the beam splitter 104 having a function of bending the optical axes are not shown.

In the first illumination optical system 100, light emitted from the light source 101 is collected by the collector lens 103 and emitted toward a sample surface, where the cells and the like as imaging objects are present, via the condenser lens 106. The sample surface is a well bottom surface Wb (see FIGS. 3A and 3B, etc.) in normal use. The collector lens 103 focuses an image of the light source 101 between the collector lens 103 and the condenser lens 107. Specifically, a light source image C1 is formed between the collector lens 103 and the condenser lens 106. Further, the collector lens 103 and the condenser lens 106 are arranged such that the light source image C1 is located at a front (light source-side) focus position of the condenser lens 106 and chief rays propagating from the condenser lens 106 toward the sample surface are parallel to an optical axis shown by a chain line. Specifically, the first illumination optical system 100 constitutes telecentric illumination.

An aperture stop 107 is arranged on a light emitting surface of the light source 101 if necessary to specify the size of the light source image C1 formed by the collector lens 103. An NA (numerical aperture) of illumination can be adjusted by the aperture stop 107. Further, a field stop 108 is arranged behind the collector lens 103 and before a conjugate point if necessary. In this way, only a range necessary for imaging can be illuminated to prevent the occurrence of flare in the imaging optical system.

In the second illumination optical system 110, light emitted from the light source 111 is collected by the collector lens 112 and emitted toward the sample surface via the condenser lens 106. The collector lens 112 is imparted with such a refraction characteristic that a light source image C2 of the light source 111 is located behind the condenser lens 106 and before the sample surface.

An aperture stop 113 is arranged on a light emitting surface of the light source 111 if necessary to specify the size of the light source image C2 formed by the collector lens 112 and the condenser lens 106. An NA of illumination can be adjusted by the aperture stop 113. Further, a field stop 114 is arranged between the collector lens 112 and the condenser lens 106 if necessary. In this way, only a range necessary for imaging can be illuminated to prevent the occurrence of flare in the imaging optical system.

The two illumination optical systems 100, 110 share the condenser lens 106. The beam splitter 104 for enabling this is provided between the collector lenses and the condenser lenses of the illumination optical systems 100, 110. More specifically, the beam splitter 104 is arranged at a position to satisfy conditions that the beam splitter 104 is behind the collector lens 103 (field stop 108 if the field stop 108 is provided) and before the condenser lens 106 in the first illumination optical system 100 and behind the collector lens 112 (field stop 114 if the field stop 114 is provided) and before the condenser lens 106 in the second illumination optical system 110.

Referring back to FIG. 1, the description of the imaging apparatus 1 is continued. The imager 13 for imaging the imaging objects such as cells and the like in the wells W is provided below the well plate WP held by the holder 12. In the imager 13, an objective lens 131 is arranged at a position right below the well plate WP. An optical axis of the objective lens 131 extends in a vertical downward direction and is coaxial with the optical axes of the first and second illumination optical systems 100, 110. Light emitted from the illuminator 10 and incident on the liquid surface from above the well W illuminates the imaging objects and light transmitted downward from the bottom surface of the well W is incident on the objective lens 131. A low magnification afocal system 132 and a high magnification afocal system 133 are switchably provided below the objective lens 131.

Specifically, the low magnification afocal system 132 and the high magnification afocal system 133 are integrally movable in a horizontal direction by an unillustrated drive mechanism, and one thereof is selectively positioned at a position right below the objective lens 131. In a state where the high magnification afocal system 133 is positioned at the position right below the objective lens 131 as shown in solid line in FIG. 1, a high magnification imaging optical system including the objective lens 131 and the high magnification afocal system 133 is configured. At this time, a relatively narrow range of the imaging objects can be imaged at a high magnification. On the other hand, in a state where the low magnification afocal system 132 is positioned at the position right below the objective lens 131 as shown in dotted line in FIG. 1, a low magnification imaging optical system including the objective lens 131 and the low magnification afocal system 132 is configured. At this time, a relatively wide range of the imaging objects can be imaged at a low magnification.

Light emitted from the low magnification afocal system 132 or the high magnification afocal system 133 is reflected by a reflecting mirror 134 and incident on an imaging element 136 via a focusing lens 135. As described later, the imaging optical system composed of the objective lens 131, the low magnification afocal system 132, the focusing lens 135 and the like has an object-side hypercentric optical property. On the other hand, the imaging optical system composed of the objective lens 131, the high magnification afocal system 133, the focusing lens 135 and the like has an object-side telecentric optical property.

The imaging element 136 is an area image sensor having a two-dimensional light receiving surface and a CCD sensor or a CMOS sensor can be, for example, used. An image of imaging objects focused on the light receiving surface of the imaging element 136 by the focusing lens 135 is imaged by the imaging element. The imaging element 136 converts the received optical image into an electrical signal and outputs it as an image signal. In such an imaging method, cells and the like as the imaging objects can be imaged in a non-contact, non-destructive and non-invasive manner and damage on the cells and the like by imaging can be suppressed. The operation of each part of the imager 13 is controlled by an imaging controller 143 provided in the controller 14.

The image signal output from the imaging element 136 is send to the controller 14. Specifically, the image signal is input to an AD converter (A/D) 144 provided in the controller 14 and converted into digital image data. The CPU 141 performs appropriate image processings based on the received image data. The controller 14 further includes an image memory 147 for storing and saving image data and a memory 148 for storing and saving programs to be executed by the CPU 141 and data generated by the CPU 141, but these may be integrated. Further, the image memory 147 and the memory 148 may be realized by appropriately combining a high-capacity storage and a semiconductor memory. The CPU 141 performs various imaging processings and arithmetic processings by executing a control program stored in the memory 148 and operating each part of the apparatus.

The imager 13 is moved in the horizontal and vertical directions by a mechanism controller 145 provided in the controller 14. Specifically, the mechanism controller 145 operates a drive mechanism 15 based on a control command from the CPU 141 to move the imager 13 in the horizontal direction, whereby the imager 13 moves in the horizontal direction relative to the wells W. Further, focusing is performed by moving the imager 13 in the vertical direction. When imaging is performed with one well W entirely contained in an imaging field of view, the mechanism controller 145 positions the imager 13 in the horizontal direction such that the optical axis of the objective lens 131 coincides with a center of this well W.

Further, the drive mechanism 15 relatively moves the illuminator 10 integrally with the imager 13 as shown by dotted line arrows in FIG. 1 when the imager 13 is moved in the horizontal direction. Specifically, the illuminator 10 is arranged such that a center of emitted light substantially coincides with the optical axis of the objective lens 131. When the imager 13 moves in the horizontal direction, the illuminator 10 moves in conjunction with the imager 13. In this way, a center of a beam of light from the illuminator 10 is constantly located on the optical axis of the objective lens 131 regardless of which well W is to be imaged, wherefore imaging conditions can be maintained to be satisfactory by making illumination conditions constant for each well W.

Besides, the controller 14 is provided with an interface (IF) unit 142. The interface unit 142 has a function of performing data exchange with an external apparatus connected via a communication line besides a user interface function of receiving an operation input from a user and presenting information such as processing results to the user. Although not shown, an input receiver for receiving the operation input from the user and a display for displaying and outputting a message, a processing result and the like from the user are connected to the interface unit 142 to realize the user interface function.

Note that the configuration of the controller 14 mentioned here is basically the same as that of a general computer device. Accordingly, the controller 14 provided in the imaging apparatus 1 may be a dedicated device with the hardware described above or may be a general-purpose processing device such as a personal computer or a work station incorporated with a control program for realizing a processing function to be described later. Specifically, a general-purpose computer device can be utilized as the controller 14 of this imaging apparatus 1. In the case of using the general-purpose computer device, it is sufficient to provide the imaging apparatus 1 with control functions minimum necessary to operate each part such as the imager 13.

Figure 3A:
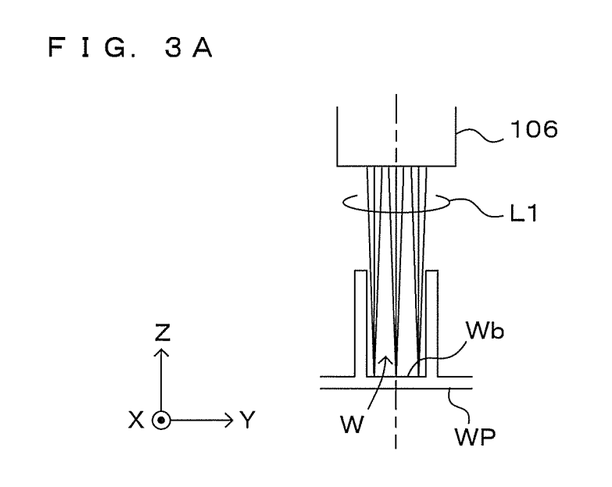
FIGS. 3A and 3B are diagrams showing illumination lights emitted from the first and second illumination optical systems.
Figure 3B:
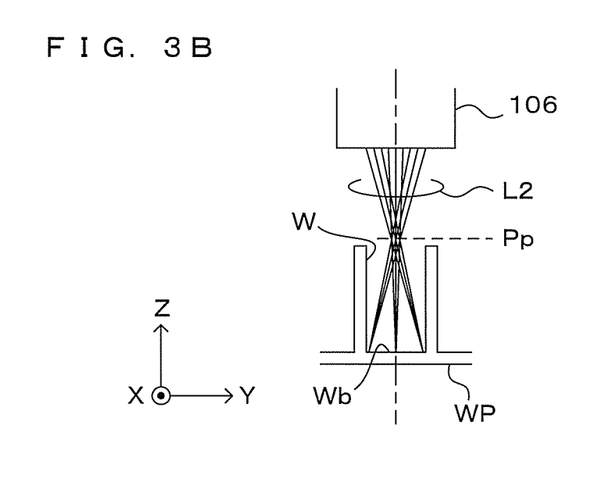

FIGS. 3A and 3B are diagrams showing illumination lights emitted from the first and second illumination optical systems. More specifically, FIG. 3A shows first illumination light L1 emitted from the first illumination optical system 100 and FIG. 3B shows second illumination light L2 emitted from the second illumination optical system 110. As shown in FIG. 3A, the first illumination light L1 emitted from the condenser lens 106 in the first illumination optical system 100 using the light source 101 as a light source is incident in a state where chief rays are incident in a parallel state on the bottom surface Wb of the well W as the sample surface on which the imaging objects are distributed. Specifically, the first illumination optical system 100 constitutes telecentric illumination whose exit pupil position is at infinity.

On the other hand, the second illumination light L2 emitted from the condenser lens 106 in the second illumination optical system 110 using the light source 111 as a light source propagates in a direction toward the optical axis of the second illumination optical system 110 and intersects with the optical axis above the well bottom surface Wb, i.e. on a front side when viewed from the illumination optical system. Specifically, an exit pupil position Pp where an image of the light source 111 (more strictly, aperture stop 113) is focused on the optical path of the second illumination optical system L2 is located at a position closer than the well bottom surface Wb as the sample surface on which the imaging objects are distributed when viewed from the second illumination optical system 110.

More specifically, under illumination by the second illumination optical system 110, the image of the light source 111 is focused between an output end of the condenser lens 106 emitting the illumination light L2 and the objective lens 131 of the imaging optical system. That is, a conjugate point for the light source 111 is located at this position. The holder 12 holds the well plate WP such that the well bottom surface Wb as the sample surface on which the imaging objects are distributed is located between this conjugate point and the objective lens 131. Thus, a chief ray of the illumination light incident on the well bottom surface Wb has a direction component in a direction away from the optical axes of the second illumination optical system 110 and the objective lens 131. In the second illumination optical system 110, the exit pupil position, the position of the image of the light source 111 and the position of the conjugate point for the light source 111 coincide.

As just described, the exit pupil positions differ from each other in the two illumination optical systems 100, 110 and these are properly used according to need in imaging the well W as described later. Note that stroboscopic illumination is used in imaging. That is, the illumination light is emitted only for a short time when imaging by the imager 13 is performed. Thus, the light source controller 146 can realize the switch of the illumination light by selecting which of the two light sources 101, 111 is to be turned on. A specific mode of properly using one of these illumination optical systems 100, 110 is described below.

Figure 4A:
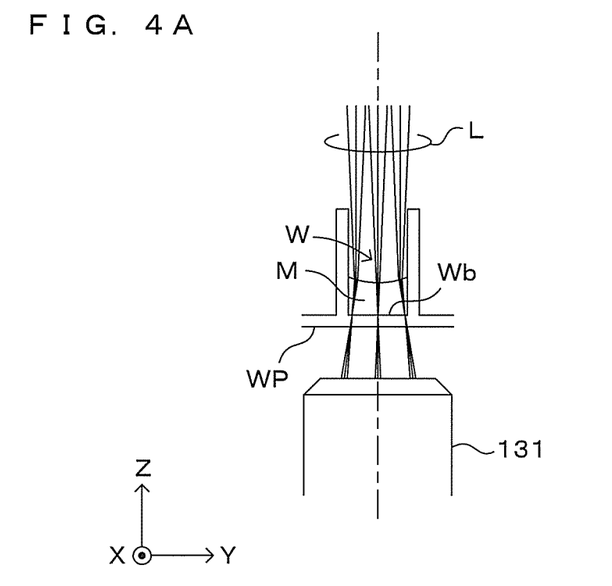
FIGS. 4A and 4B are diagrams showing a state at the time of imaging the well.
Figure 4B:
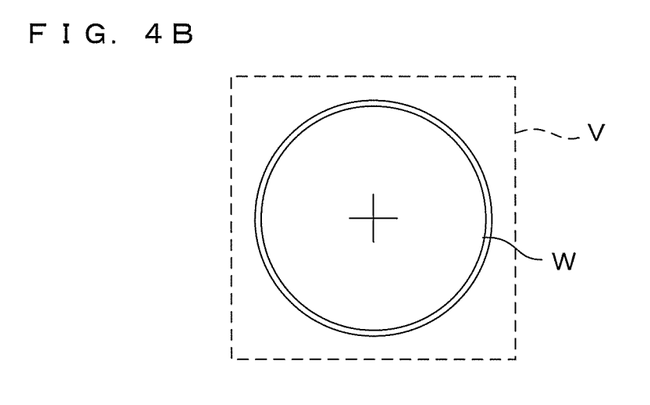

FIGS. 4A and 4B are diagrams showing a state at the time of imaging the well. More specifically, FIG. 4A is a diagram showing a propagation path of light at the time of imaging the well and FIG. 4B is a diagram showing a relationship of the well and the imaging field of view. The medium M poured in a liquid state is in the well W carrying the cells and the like as the imaging objects. Thus, the illumination light L incident from above the well W is incident on the well bottom surface Wb (sample surface), where the imaging objects are present, via the liquid surface of the medium M. The liquid surface generally forms an upward concave meniscus, whereby the illumination light L is refracted and bent outwardly from the center of the well W. Refraction is small near the center of the well W and becomes larger toward the peripheral edge part of the well W.

The imaging optical system including the objective lens 131 constitutes an object-side hypercentric optical system and has a function of efficiently collecting the light bent outwardly in this way and guiding it to the imaging element 136. Specifically, light incident obliquely outwardly can be focused on the imaging element 136 at a position distant from the optical axis of the lens. Thus, this imaging optical system is suitable when one well W is imaged while being entirely contained in an imaging field of view V as shown in FIG. 4B. This point is as disclosed also in JP 2015-118036A.

One well W can be entirely contained in the imaging field of view V as shown in FIG. 4B when the well W having a relatively small opening diameter is imaged at a low magnification. On the other hand, such as in the case of imaging imaging objects carried in a well having a large opening diameter (e.g. well on a well plate with six wells), the size of an area to be imaged becomes relatively larger than that of the imaging field of view and it may not be possible to contain the entire well W in the imaging field of view V.

Figure 5:
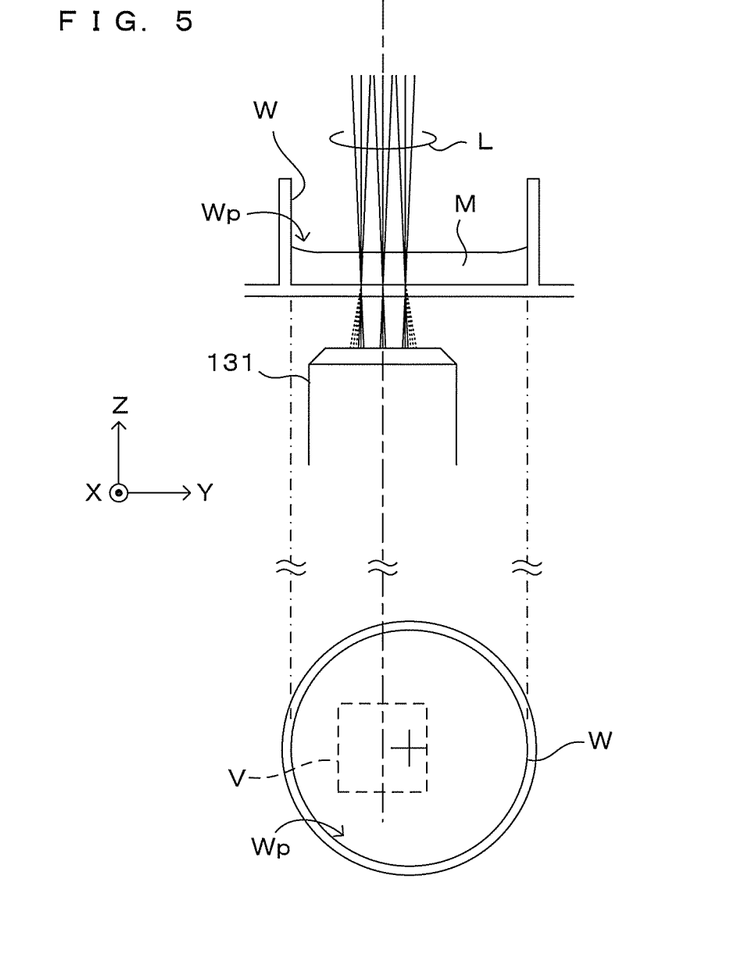
FIGS. 5 and 6 are diagrams showing a state of imaging when the size of the well is larger than that of the imaging field of view.
Figure 6:
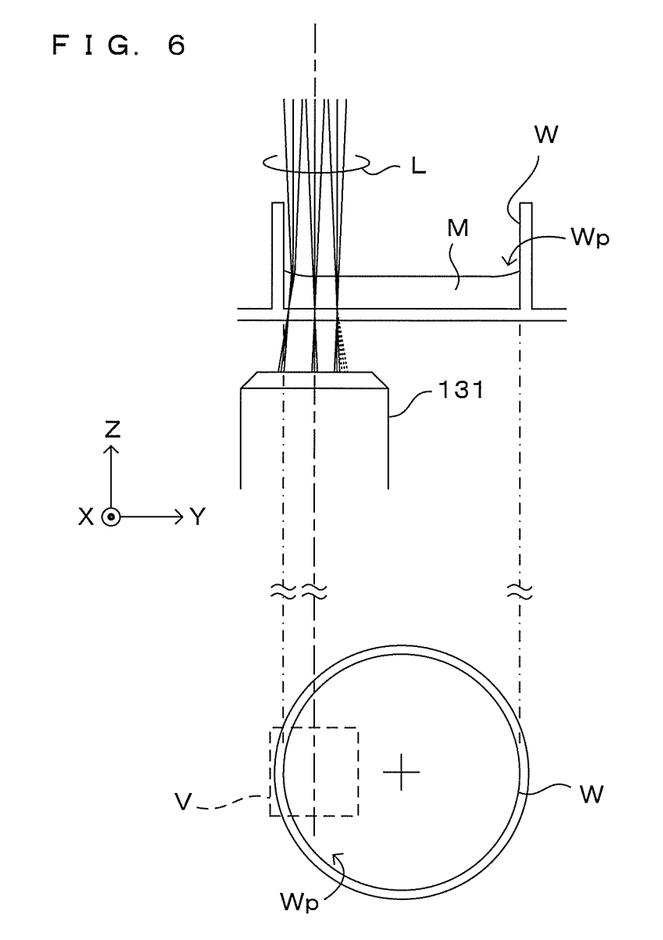

FIGS. 5 and 6 are diagrams showing a state of imaging when the size of the well is larger than that of the imaging field of view. More specifically, FIG. 5 shows imaging when the well peripheral edge part is not contained in the imaging field of view and FIG. 6 shows imaging when the well peripheral edge part is contained in the imaging field of view. Here is described a case where the well W having a larger opening diameter than that described thus far is imaged at a low magnification. For example, a similar way of thinking can be applied when the size of an area to be imaged is larger than that of the imaging field of view V such as when imaging objects carried in a shallow container having a large opening diameter called a dish are imaged.

When the area to be imaged is wider than the imaging field of view V, it is considered to generate an image representing the entire area to be imaged by imaging and dividing this area into a plurality of images and combining those images by image processings. In this case, the individual images before synthesis need to have better quality to ensure desired image quality of the generated image. Points of concern for this are described next.

When the imaging field of view V contains only a central area distant from a peripheral edge part Wp of the well W as shown in FIG. 5, the influence of the meniscus on the surface of the medium M on the optical path is sufficiently small. Thus, in telecentric illumination, light incident near the optical axis of the objective lens 131 is collected and incident on the imaging element 136, whereas a mismatch occurs due to a difference in inclination between the incident light and the chief rays of the optical system at positions distant from the optical axis.

Specifically, at the positions distant from the optical axis, light whose chief rays are inclined outwardly as shown in dotted line in FIG. 5 is received, assuming refraction on the liquid surface on the side of the objective lens 131, whereas the light transmitted through the well W propagates straight without being subjected to refraction by the meniscus, wherefore the inclinations of the chief rays in the incident light and those of the chief rays on a light receiving side do not coincide. How the image looks may change due to this, particularly due to the degradation of image quality in the peripheral edge part of the imaging field of view V, specifically due to a dark image or the incidence of the illumination light only in partial directions of a light collection range of the objective lens.

On the other hand, when the imaging field of view V is set in an area including the peripheral edge part Wp of the well W or an area very close to this as shown in FIG. 6, the inclinations of the chief rays of the light refracted by the meniscus and those of the chief rays on the light receiving side substantially coincide and light can be efficiently collected near the well peripheral edge part Wp. Contrary to this, in a part near the well central part on a side opposite to the well peripheral edge part Wp across the optical axis of the objective lens 131, image quality is, of course, degraded since the light propagating straight is incident on the objective lens 131 having the inclinations of the chief rays assuming refraction by the meniscus as in the case of FIG. 5.

If an area capable of ensuring necessary image quality out of the physical imaging field of view V of the imager 13 is considered to be an effective imaging field of view, the effective imaging field of view becomes narrower when the area in the imaging field of view is not affected by the meniscus as described above in the combination of telecentric illumination and the hypercentric imaging optical system. Accordingly, in this embodiment, the second illumination optical system 110 capable of obtaining good image quality in the absence of the influence of the meniscus is provided separately from the first illumination optical system 100 constituting telecentric illumination.

Figure 7:
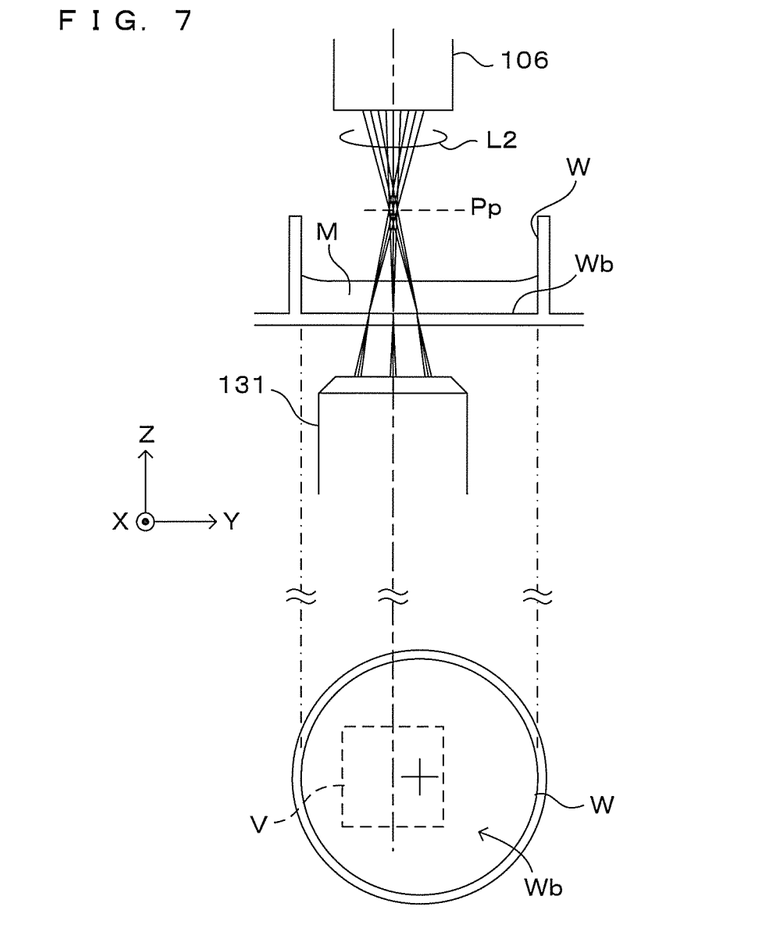
FIG. 7 is a diagram showing imaging using the second illumination optical system.

FIG. 7 is a diagram showing imaging using the second illumination optical system. As described above, the illumination light L2 emitted from the condenser lens 106 in the second illumination optical system 110 is such that the chief rays are inclined in the directions toward the optical axis. Thus, in the absence of the influence of the meniscus, the chief rays of the illumination light incident on the bottom surface Wb of the well W are not parallel to each other. Since the exit pupil position Pp of the second illumination optical system 110 is located before the well bottom surface Wb when viewed from the second illumination optical system 110 in this embodiment, the chief rays spread outwardly from the optical axis of the objective lens 131 in the illumination light L2 incident on the well bottom surface Wb.

If the inclinations of the chief rays at this time are set to coincide with those of the chief rays on the side of the objective lens 131, the light transmitted through the well bottom surface Wb is collected by the objective lens 131 and finally guided to the imaging element 136 as shown in FIG. 7. Thus, imaging can be performed with good image quality in the entire imaging field of view V and the entire physical imaging field of view V can be utilized as the effective imaging field of view.

In terms of adjusting an incident direction of the illumination light in accordance with the properties of the imaging optical system, it is, in principle, possible to obtain similar effects, for example, by arranging a point light source at the exit pupil position of the objective lens 131. However, this is not realistic since problems such as the interference of the light source and the well plate WP and the alteration of the samples due to heat emitted from the light source may occur due to the necessity to arrange the point light source at a position right above the sample surface.

If the above illumination is constituted by the illumination optical system for relaying the light emitted from the light source 111 by a plurality of lenses as in the above embodiment, it is possible to realize an illumination optical system optimized according to the properties of the imaging optical system by appropriately combining the lenses, the stops and the like. For example, if the conjugate point of the light source 111 in the illumination optical system 110 and the exit pupil position of the objective lens 131 are set to coincide, the illumination light propagating in the direction away from the optical axis beyond the conjugate point can be efficiently guided to the imaging element 136 by the objective lens 131.

As just described, in the imaging apparatus 1 of this embodiment, the first illumination optical system 100 suitable for imaging the area subjected to the influence of the meniscus and the second illumination optical system 110 suitable for imaging the area free from the influence of the meniscus are equipped as the illumination optical systems to be combined with the imaging optical system having the hypercentric property. When it is necessary to image an area wider than the imaging field of view V of the imager 13, a plurality of images are imaged by properly using the illumination optical systems for the areas with and without the influence of the meniscus, whereby the quality of an image obtained by combining these images can be made satisfactory.

Figure 8A:
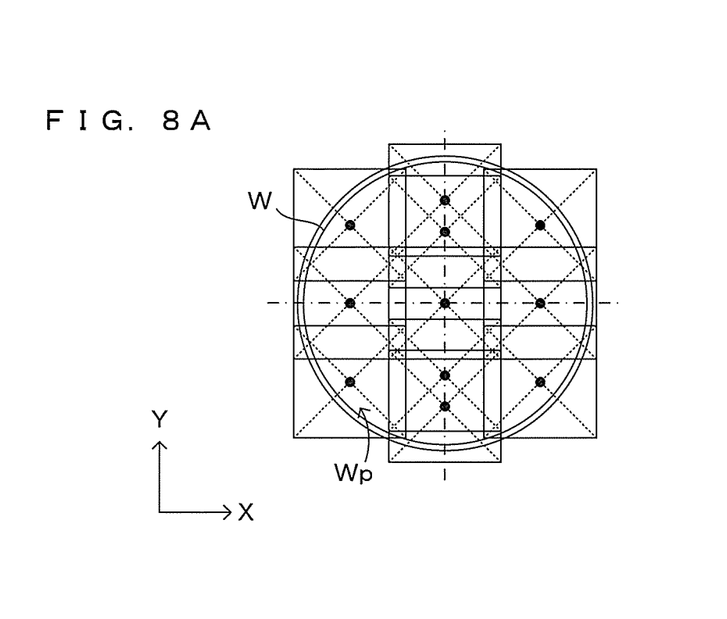
FIGS. 8A and 8B are diagrams illustrating a method for dividing one well into a plurality of images.
Figure 8B:
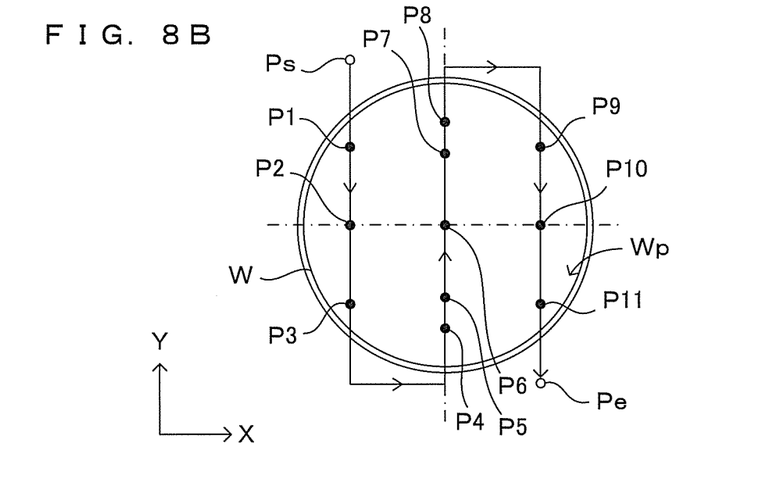

FIGS. 8A and 8B are diagrams illustrating a method for dividing one well into a plurality of images. More specifically, FIG. 8A shows an example of allocating images in dividing the well W into a plurality of images and FIG. 8B is a diagram showing a scanning path of the imager 13 to obtain such images. In FIG. 8A, each of the plurality of images covering the entire well W by partially overlapping each other is shown by a solid-line rectangle, diagonals of each rectangle are shown in dotted line and a centroid position thereof is shown by a black circle to make the plurality of rectangles easily distinguishable. The centroid position of the rectangle corresponds to a position where the optical axis of the objective lens 131 intersects with the well bottom surface Wb during imaging.

In the allocation example shown in FIG. 8A, the entire well W is divided into eleven images. In the central part of the well W, the arrangement of the image is set not to include the well peripheral edge part Wp in the imaging field of view. The image not including the well peripheral edge part Wp in this way is supposed to be imaged using the second illumination optical system 110. On the other hand, the image imaged to include the well peripheral edge part Wp in the imaging field of view is arranged such that at least a centroid of the image is located in the well W. Imaging is supposed to be performed using the first illumination optical system 100. By doing so, a difference in the inclinations of the chief rays can be reduced between the illumination side and the light receiving side at an outer side of the centroid position (side close to the well peripheral edge part Wp) and image quality degradation can be suppressed.

FIG. 8B shows an example of a movement path of the imager 13 in dividing and imaging the well W into the plurality of images. In the imaging apparatus 1 of this embodiment, the imager 13 and the illuminator 10 integrally horizontally move relative to the well plate WP placed on the holder 12. The plurality of images shown in FIG. 8A can be obtained by performing imaging at appropriate relative positions while moving the imager 13 in the X and Y directions along the bottom surface of the well plate WP. FIG. 8B shows the scanning movement path of the imager 13 at this time, more precisely a locus of the intersection of the optical axis of the objective lens 131 provided in the imager 13 and the well bottom surface Wb.

Points P1 to P11 indicated by black circles respectively correspond to the centroid positions of the plurality of images shown in FIG. 8A. Further, since the centroid position of each image is also the position of the optical axis of the objective lens 131 when this image is imaged, necessary images can be obtained by a series of scanning movements if a scanning movement recipe of the imager 13 (and the illuminator 10) is prepared such that the optical axis of the objective lens 131 successively passes through these points P1 to P11 and imaging by the imager 13 is performed when the optical axis position of the objective lens 131 reaches these points P1 to P11. In this sense, the positions of the imager 13 corresponding to the points P1 to P11 are referred to as "imaging positions". If the allocation of the images is determined, the imaging positions can be set according to that. Further, Ps and Pe denote a start point and an end point of the optical axis position of the objective lens 131 in the scanning movement of the imager 13, respectively.

Figure 9:
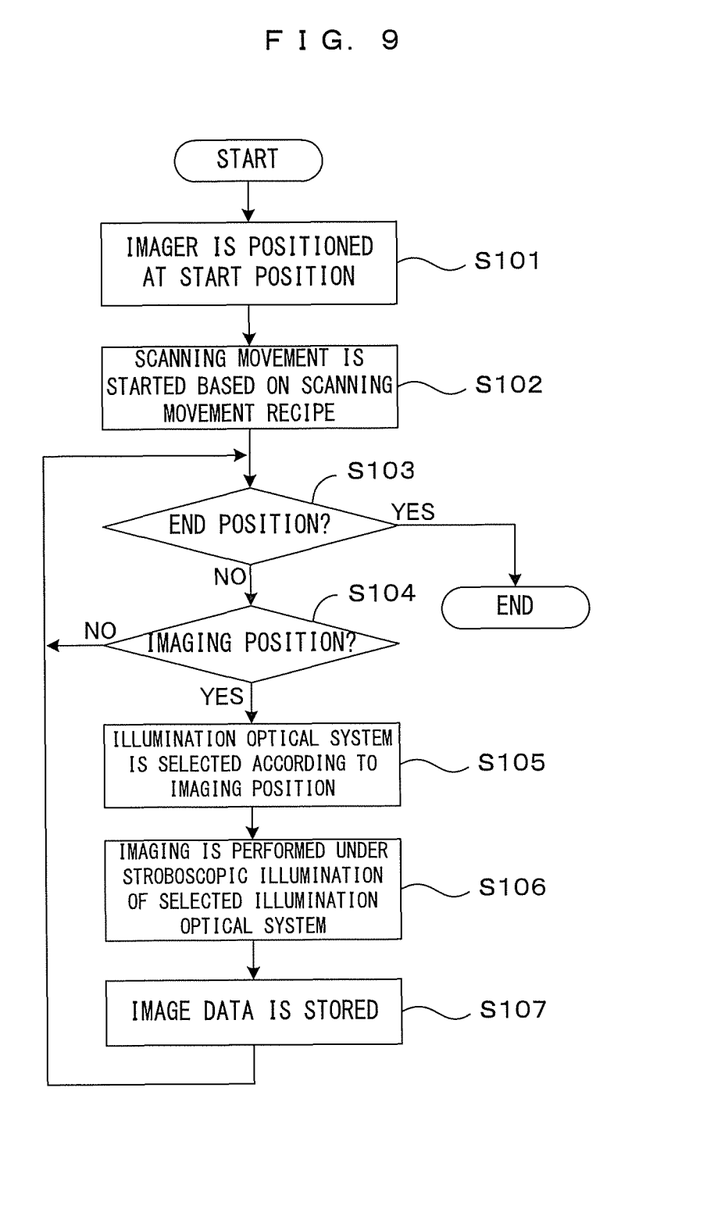
FIG. 9 is a flow chart showing an imaging process in this embodiment.

FIG. 9 is a flow chart showing an imaging process in this embodiment. The CPU 141 performs the imaging process shown in FIG. 9 by causing each part of the apparatus to perform a predetermined operation based on the control program prepared in advance, whereby a plurality of images, for example, shown in FIG. 8A are obtained. First, the imager 13 is positioned at a predetermined start position by the drive mechanism 15 that operates according to a control command from the mechanism controller 145 (Step S101). The start point Ps shown in FIG. 8B corresponds to the optical axis position of the objective lens 131 at this time. Note that although only the scanning movement of the imager 13 is described here, the illumination light 10 also moves according to the movement of the imager 13 such that the center of the illumination light and the optical axis of the objective lens 131 constantly coincide as described above.

Subsequently, the scanning movement of the imager 13 relative to the well W is started based on the scanning movement recipe set in advance (Step S102). When the imager 13 reaches an end position corresponding to the end point Ps, the process is finished (Step S103). Until the end position is reached, Steps S105 to S107 are performed for imaging every time the imager 13 reaches any one of the imaging positions corresponding to the points P1 to P11 (Step S104). At which position the imager 13 is located can be detected, for example, based on an output signal from a position sensor (not shown) mounted in the imager 13.

Specifically, the illumination optical system is selected according to the imaging position where the imager 13 is currently located (Step S105). Specifically, the first illumination optical system 100 is selected if the well peripheral edge part Wp is included in the imaging field of view V at the current position of the imager 13 and the second illumination optical system 110 is selected if the well peripheral edge part Wp is not included. In the example shown in FIGS. 8A and 8B, the second illumination optical system 110 is selected at the imaging positions corresponding to the points P5 to P7 and the first illumination optical system 100 is selected at the imaging positions corresponding to the other points P1 to P4 and P8 to P11. As just described, the selective arrangement of the illumination optical systems 100, 110 corresponds to an example of an "arranging step" of the invention.

Subsequently, the imaging objects are stroboscopically illuminated by lighting the light source of the selected illumination optical system for a predetermined time and, simultaneously with this, the imaging element 136 performs imaging, whereby one image is obtained (Step S106: imaging step). Image data obtained by digitizing an image signal output from the imaging element 136 by the AD converter 144 is stored in the image memory 147 (Step S107). By repeating the above process until the imager 13 reaches the end position, imaging is performed at the imaging position corresponding to each of the points P1 to P11 and eleven images are obtained.

Since imaging is performed under stroboscopic illumination, the scanning movement of the imager 13 needs not be temporarily stopped for imaging and the drive mechanism 15 may scan and move the imager 13 at a constant speed in accordance with the scanning movement recipe. By optimizing the scanning movement recipe to minimize a length of the path connecting the respective points P1 to P11, a time required for imaging can be shortened.

Out of the plurality of images thus obtained, those including the well peripheral edge part Wp are imaged under illumination by the first illumination optical system and those not including the well peripheral edge part Wp are imaged under illumination by the second illumination optical system 110. Thus, in each image, a reduction of image quality due to the presence or absence of the meniscus and a mismatch with the illumination optical system is suppressed. The image of the entire well W can be generated with good quality by extracting and combining parts with good image quality from the respective images. In an area where the plurality of images overlap, the image having better image quality may be adopted in view of the position of this area in the well W and the used illumination optical system.

As described above, in this embodiment, two illumination optical systems 100, 110 are provided. the illumination optical system 100 is corresponding to the case where the influence of the meniscus is present in the imaging field of view V of the imager 13 while the illumination optical system 110 is corresponding to the case free from the influence of the meniscus. Imaging is performed while those illumination optical systems are switched according to the imaging position. By doing so, images with good image quality can be obtained in both the areas with the influence of the meniscus and those without the influence of the meniscus out of the areas to be imaged.

As described above, in the imaging apparatus 1 of this embodiment, the illuminator 10 functions as an "illuminator" of the invention and the holder 12 functions as a "holder" of the invention. Further, a combination of the objective lens 131, the focusing lens 136, the high magnification afocal system 132 and the high magnification afocal system 133 corresponds to an "imaging optical system" of the invention and the imaging element 136 functions as an "imaging element" of the invention. In the illuminator 10, the light source 111 corresponds to a "light source" of the invention, and the second illumination optical system 110 corresponds to an "illumination optical system" of the invention. The light source 101 corresponds to "another light source" of the invention and the collector lens 103 functions as "another collector lens" of the invention. The light source controller 146 functions as a "light source controller" of the invention. In the above embodiment, the well plate WP corresponds to a "sample container" of the invention.

Note that the invention is not limited to the above embodiment and various changes other than those described above can be made without departing from the gist of the invention. For example, in the above embodiment, two types of illumination optical systems 100, 110 having different exit pupil positions are provided and switchingly used. However, in line with the gist of the invention, only the second illumination optical system 110 may be provided as the illuminator.

Further, for example, two illumination optical systems may be configured by a single light source and two optical systems although two light sources 101, 111 are provided in correspondence with the two illumination optical systems 100, 110 in the above embodiment. Further, although some of the members constituting the two illumination optical systems are shared in the above embodiment, completely independent two illumination optical systems may be provided. A plurality of second illumination optical systems having mutually different exit pupil positions may be provided.

Further, the allocation of the images in the above imaging process is merely for description, and an actual arrangement is not limited to this. Further, although the case of imaging only one well is described in the above allocation example, the scanning movement recipe may be so configured that a plurality of wells can be collectively imaged by a series of scanning movements.

As described above, according to the invention, an image with good image quality can be obtained for the imaging object in the absence of the influence of meniscus by combining the illumination optical system for causing a beam having components in directions away from the optical axis to be incident on the sample surface and the imaging optical system capable of causing the light having such direction components to be satisfactorily incident on the imaging element.

Further, as described by way of the specific embodiment, the invention may be configured such that the exit pupil position of the illumination optical system and an entrance pupil position of the imaging optical system coincide in the invention. In such a configuration, illumination light spreading in directions away from the optical axis beyond the exit pupil position can be efficiently collected by the imaging optical system and received by the imaging element. In this way, a bright image can be obtained.

Further, for example, a numerical aperture of the illumination optical system may be equal to or larger than that of the imaging optical system. In such a configuration, even if the inclination of the illumination light changes such as due a small inclination of a liquid surface, the illumination light can satisfy the numerical aperture of the imaging optical system and a reduction of light quantity and light quantity unevenness in an imaging field of view can be prevented.

Further, for example, the illumination optical system may be configured to include a collector lens for collecting light from the light source and a condenser lens for collecting the light emitted from the collector lens and emitting the collected light toward the sample surface. According to such a configuration, illumination corresponding to properties of various imaging optical systems is easily realized by combining these optical elements having appropriate properties.

Further, for example, the light source may include an aperture stop. According to such a configuration, an NA of illumination can be adjusted by limiting an angle range of light incident on the collector lens by the aperture stop.

Further, for example, a field stop may be provided between the collector lens and the condenser lens. According to such a configuration, stray light can be suppressed by regulating a range of illumination light incident on the sample surface, whereby the influence of flare possibly occurring in the sample and the imaging optical system can be reduced.

Further, for example, the illumination optical system may include a beam splitter provided between the collector lens and the condenser lens, another light source and another collector lens for collecting light emitted from the other light source and causing the collected light to be incident on the condenser lens via the beam splitter, the other collector lens and the condenser lens may constitute an object-side telecentric optical system and the imaging apparatus may further include a light source controller for selectively turning on the light source and the other light source. According to such a configuration, imaging can be performed with good image quality for both samples with the influence of the meniscus and those without the influence of the meniscus by selectively illuminating by the illumination light having the above properties and telecentric illumination light.

Besides, the configuration of the illumination optical system is not limited to the above one within a range matching the technical concept of the invention, and various configurations such as the one in which the aperture stop is arranged at a position distant from the light source and the one further including a relay lens can be used.

This invention can be suitably applied to imaging apparatuses for imaging various raw samples such as cells, cell colonies, spheroids, bacteria, lesion tissues and microorganisms.

Although the invention has been described with reference to specific embodiments, this description is not meant to be construed in a limiting sense. Various modifications of the disclosed embodiment, as well as other embodiments of the invention, will become apparent to persons skilled in the art upon reference to the description of the invention. It is therefore contemplated that the appended claims will cover any such modifications or embodiments as fall within the true scope of the invention.

What is claimed is:

1. An imaging apparatus that images a raw sample as an imaging object carried together with liquid in a sample container, the apparatus comprising:
   a holder that holds the sample container;
   an imaging optical system, arranged to face the sample container held by the holder, that has an object-side hypercentric property;
   an imaging element that images an image of the imaging object focused by the imaging optical system; and
   an illuminator that illuminates the imaging object from a side opposite to the imaging optical system across the sample container held by the holder, wherein:
   the illuminator includes a light source and an illumination optical system that causes light emitted from the light source to be incident on a sample surface where the imaging object is present;
   the illumination optical system has an optical axis coaxial with that of the imaging optical system and an exit pupil position located between the illumination optical system and the imaging optical system;
   the holder arranges the sample surface between the exit pupil position and the imaging optical system;
   the sample container contains a well with a bottom surface having optical transparency;
   the well carries the raw sample as the imaging object together with the liquid;
   a size of an imaging field of view of the imaging apparatus is smaller than a size of the bottom surface of the well; and
   the imaging field of view covers only a central area of the well, the central area being distant from a peripheral edge of the well.

2. The imaging apparatus according to claim 1, wherein the exit pupil position of the illumination optical system and an entrance pupil position of the imaging optical system coincide with each other.

3. The imaging apparatus according to claim 1, wherein a numerical aperture of the illumination optical system is equal to or larger than that of the imaging optical system.

4. The imaging apparatus according to claim 1, wherein the illumination optical system includes a collector lens that collects light from the light source and a condenser lens that collects the light emitted from the collector lens and emits the collected light toward the sample surface.

5. The imaging apparatus according to claim 4, wherein the light source includes an aperture stop.

6. The imaging apparatus according to claim 4, further comprising a field stop provided between the collector lens and the condenser lens.

7. An imaging apparatus that images a raw sample as an imaging object carried together with liquid in a sample container with a bottom surface having optical transparency, the apparatus comprising:
- a holder that holds the sample container;
- an imaging optical system, arranged to face the sample container held by the holder, that has an object-side hypercentric property;
- an imaging element that images an image of the imaging object focused by the imaging optical system; and
- an illuminator that illuminates the imaging object from a side opposite to the imaging optical system across the sample container held by the holder, wherein:
- the illuminator includes a light source and an illumination optical system that causes light emitted from the light source to be incident on a sample surface where the imaging object is present;
- the illumination optical system has an optical axis coaxial with that of the imaging optical system and an exit pupil position located between the illumination optical system and the imaging optical system;
- the holder arranges the sample surface between the exit pupil position and the imaging optical system;
- the illumination optical system includes a collector lens that collects light from the light source and a condenser lens that collects the light emitted from the collector lens and emits the collected light toward the sample surface;
- the imaging apparatus further comprises a light source controller;
- the illumination optical system includes a beam splitter provided between the collector lens and the condenser lens, another light source and another collector lens that collects light emitted from the other light source and causing the collected light to be incident on the condenser lens via the beam splitter;
- the other collector lens and the condenser lens constitute an object-side telecentric optical system; and
- the light source controller selectively turns on the light source and the other light source.

8. The imaging apparatus according to claim 7, wherein the exit pupil position of the illumination optical system and an entrance pupil position of the imaging optical system coincide with each other.

9. The imaging apparatus according to claim 7, wherein the light source includes an aperture stop.

10. The imaging apparatus according to claim 7, further comprising a field stop provided between the collector lens and the condenser lens.

* * * * *